United States Patent [19]

Oshinsky

[11] Patent Number: 5,069,876
[45] Date of Patent: Dec. 3, 1991

[54] COMBINED SCENT AND AUDIO POINT OF SALE DISPLAY UNIT

[76] Inventor: Candace Oshinsky, 650 Thomas Ave., Baldwin, N.Y. 11510

[21] Appl. No.: 528,712

[22] Filed: May 24, 1990

[51] Int. Cl.$^5$ .......................... A61L 9/00; G09F 19/00
[52] U.S. Cl. ............................................ 422/4; 40/407
[58] Field of Search ............................... 422/4; 40/407

[56] References Cited

U.S. PATENT DOCUMENTS

| | | | |
|---|---|---|---|
| 2,129,368 | 9/1938 | Ballew | 40/407 |
| 2,540,144 | 2/1951 | Stern | 358/142 |
| 2,813,452 | 11/1957 | Laube | 422/4 |
| 2,905,049 | 9/1959 | Laube | 422/4 X |
| 3,795,438 | 3/1974 | Westenholz et al. | 422/4 X |
| 4,603,030 | 7/1986 | McCarthy | 422/4 |
| 4,629,604 | 12/1986 | Spector | 422/5 X |
| 4,707,338 | 11/1987 | Spector | 422/4 X |

Primary Examiner—Robert J. Warden
Assistant Examiner—Stephanie Blythe
Attorney, Agent, or Firm—Klein & Vibber

[57] ABSTRACT

A scent and audio point of sale display unit having a housing of a parallepiped shape, in which a prerecorded tape player and scent-emitting mechanism are mounted. The tape player and scent-emitting mechanism are connected to an electric power source, for example, a battery, and can be activated or deactivated simultaneously by depressing a push button mounted on the front face of the unit. Alternatively, a photocell which coacts with a light source can be used to activate the tape player and scent-emitting mechanism which then automatically deactivates itself. A loudspeaker and scent-emitting porthole are also mounted on the front face of the unit.

9 Claims, 2 Drawing Sheets

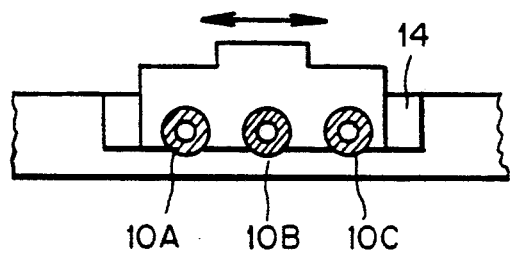
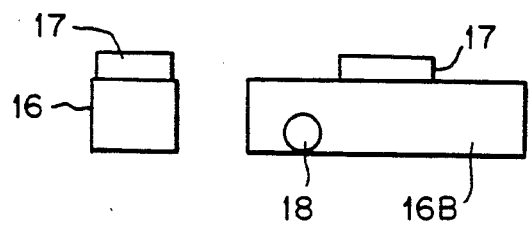
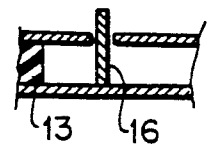
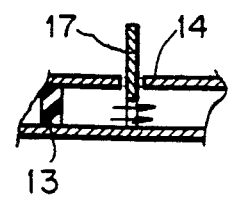
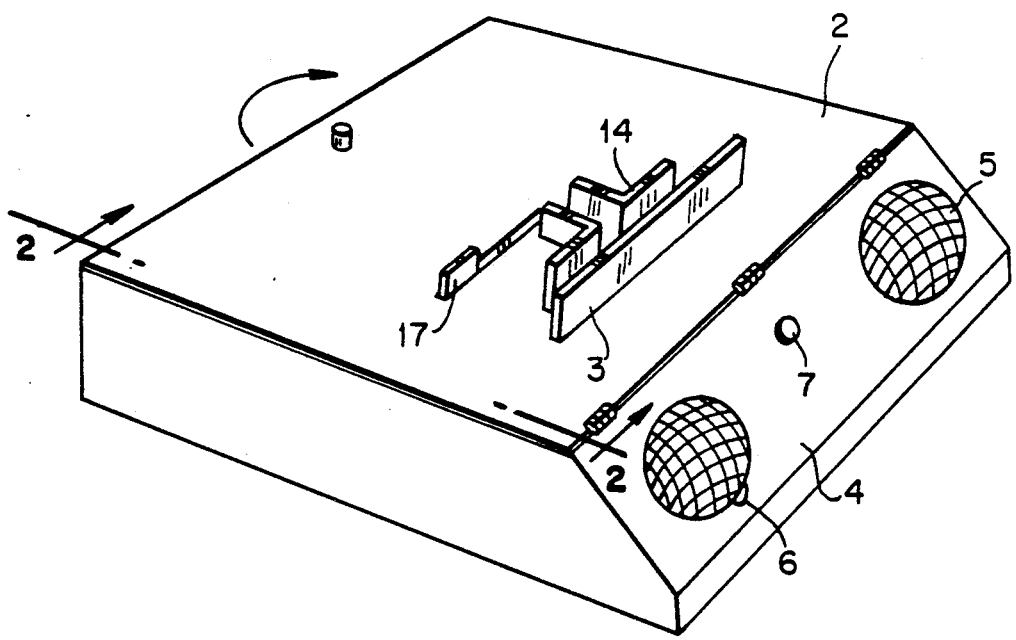

COMBINED SCENT AND AUDIO POINT OF SALE DISPLAY UNIT

BACKGROUND OF THE INVENTION

The present invention relates, generally, to a point of sale display unit which simultaneously emits a fragrance and plays a prerecorded tape message.

A variation of this point of sale display unit includes a mechanism for having a preselected one of several aromatic fragrances emitted by the unit.

It is another object of the invention to provide such a unit with a photo display stand mounted on top of the unit. The photograph for the display stand can be selectively changed, depending on which fragrance is being emitted by the unit.

The aroma of perfumes and perfume-base products was originally derived from the essential oils of plants. However, in more recent times, chemists have been able to synthesize many other essential oils, some simulating natural products, and others using altogether new scents. For example, such various essential oils, in effect, constitute powerful stimulants for the potential purchaser of a product which is being advertised by means of playing a prerecorded message by means of the sale display u it of this invention.

The relationship of scents t emotions and moods is well-established. Consequently, the emission of a preselected scent, together with the sound effect emanating from a prerecorded tape message, constitutes a powerful sales tool. The display unit of this invention is designed to utilize this interaction between scents and human responses. The arrangement of the invention also contemplates combining with the audio and scent effect a visual effect, which is achieved by means of a photograph mounted on the display unit. The photograph can be selectively changed to correspond with the preselected aroma or scent which is being emitted by the display unit.

SUMMARY OF THE INVENTION

In view of the foregoing, the main object of this invention is to provide a point of sale display unit which simultaneously emits a scent and plays a prerecorded tape.

More particularly an object of this invention is to provide a point of sale display unit which, in addition to simultaneously emitting a scent and playing a prerecorded tape, also displays a photograph mounted on top of the unit.

Yet another object of the invention is to provide an assembly, wherein a plurality of scents are stored and can be selectively projected, or blown out, when a corresponding prerecorded tape message is played.

A further object of the arrangement of the invention is to enable the person operating the unit to mount a photograph on top of the unit which corresponds to the preselected scent and audio.

Briefly stated, these objects are attained by providing an arrangement, which may be in the form of a parallepiped box made of sheet metal or plastic material. The front face of this box is preferably inclined and includes two openings, each of which is protected by a raw mesh or textile screening material. One of these openings serves to emit the air stream or burst containing a fragrance, whereas the other is a loudspeaker. A frame or stand for holding the photograph is mounted on top of this box. An actuating plunger or button, which serves to actuate a blower or pump, and a prerecorded tape player mounted inside the box, is mounted in the middle of the box.

In another embodiment of the invention, the activation of the blower or pump and prerecorded tape player is effected by means of a photocell actuating mechanism, in lieu of the plunger or button.

In yet another embodiment of the invention, a slide is adapted to selectively open and close various channels in which various scent-emitting substances are mounted. This slide is operatively mounted on top of the box. These channels are in communication with the scent-emitting porthole through which the scent carrying air is blown out, or pumped out, by way of a pump or motor mounted inside the box. A passageway to guide an air current, which passes over the essential oil or fragrance concentrate mounted in the passageway, leads to the fragrance or scent-emitting porthole. In lieu of the blower, which may take the form of a cylindrical or propeller-shaped fan, the scent-emitting means can also be in the form of a pump, preferably a diaphragm pump which expels bursts of scent-containing air. One or more preselected scents can be released by moving the slide on top of the box. The scent-emitting substances suitable for use with the display unit of this invention are of the type manufactured by F-MATIC of America of American Fork, Utah 84003. Such scent-emitting substances are generally manufactured in the form of cartridges which can easily be mounted in the passageways of the display unit. Such scent-emitting substances are generally made of hypoallergenic material, so as to be as innocuous as possible to the public at large.

DESCRIPTION OF THE DRAWING

For a better understanding of the invention, as well as of other objects and features thereof, reference is made to the following detailed description, to be read in conjunction with the accompanying drawings wherein:

FIG. 3A is a detail of the arrangement of the manual slide co-acting with the three scent-conducting pipes;

FIG. 3B is an alternate type of a manual slide shown in elevation;

FIG. 3C is an elevational view of the slide shown in FIG. 3A;

FIG. 4A is a partial cross-sectional view of one of the pipes conducting the scent stream shown in the closed position;

FIG. 4B is a cross-sectional view of the pipe carrying the scent stream shown in an open position; and FIG. 5 is an isometric perspective view showing the entire arrangement of the invention.

DESCRIPTION OF THE INVENTION

Figure 1:
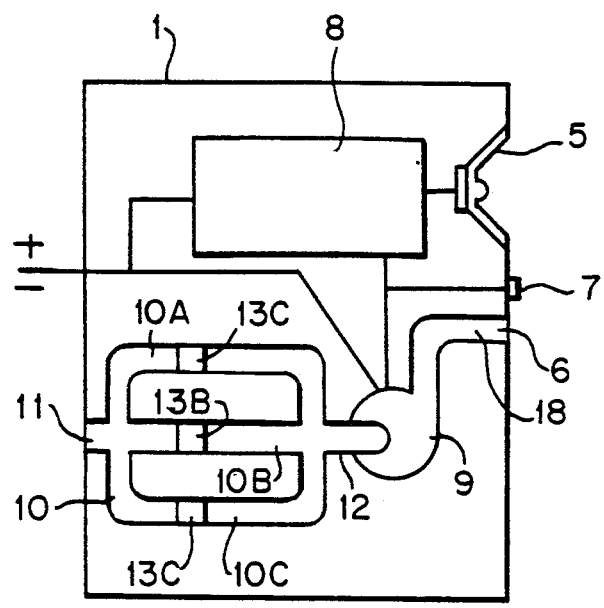
FIG. 1 is a schematic plan view of our embodiment of the arrangement of the invention.
Figure 1A:
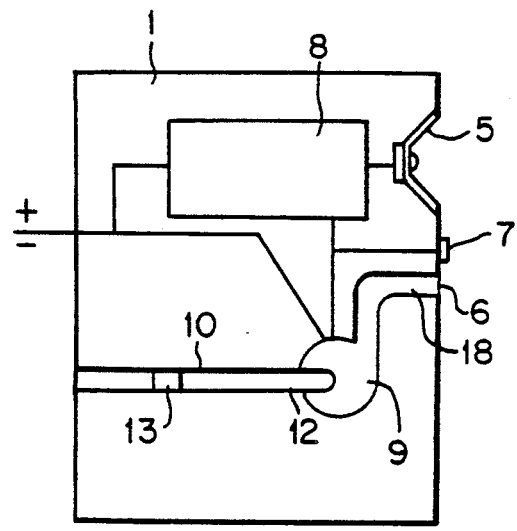
FIG. 1A is a schematic plan view of a second embodiment of the arrangement of the invention.
Figure 2:
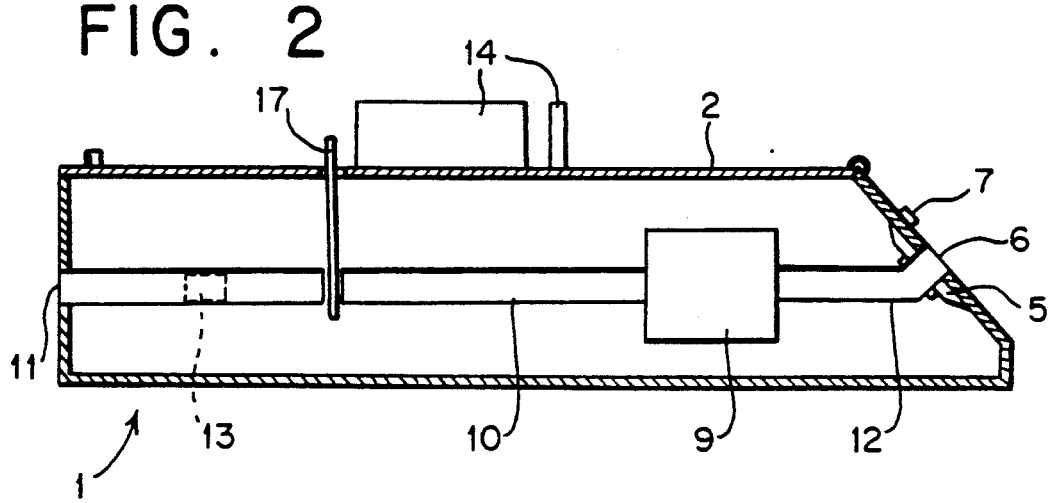
FIG. 2 is a schematic cross-sectional elevational view of the arrangement of FIG. 1 along line 2—2.

Referring now to the drawings, there is shown a scent and audio display arrangement, which includes a parallepiped box 1, having a hinged top 2, which can be pivoted forwardly, as shown in FIG. 5. On top of the hinged top 2, there is mounted a photo display stand support 3, in which a photograph (not shown), or the like, can be mounted. The box 1 has an inclined front face 4, which includes a loudspeaker 5 and a fragrance porthole 6. An actuating button 7 is mounted in the middle of the front face 4, so as to operationally activate (turn on), simultaneously, the tape recorder and player 8, as well as the pump or blower 9. The activation mechanism is conventional and cease automatically after a predetermined period of time has elapsed. The tape recorder and player 8 can be formed as a conventional answering machine mechanism, which plays back a prerecorded message upon being energized. The pump or blower 9 may also be of conventional construction. For example, the blower 9 may be a cylindrical fan or a propeller-type fan. The pump may be a conventional diaphragm pump. Both the tape recorder and player 8 and the pump or blower 9 are connected to an AC power source or a battery, as shown in FIGS. 1 and 1A. If a battery power source is used, the unit can be portable. The pump or blower 9 is connected to a scent stream supplying arrangement 10. This scent stream supplying arrangement 10 includes an air intake 11 and an outlet pipe 12. The outlet pipe 12 is in communication with the pump or blower 9, so that the pump or blower 9 produces a suction effect in the outlet pipe 12 and expels a stream of scent-containing air through the fragrance porthole 6 via the outlet pipe 13.

As can be noted from FIGS. I, 4A and 4B, the arrangement includes a three-pipe arrangement 10, wherein the air intake 11 and the outlet part 12 includes three pipes 10A, 10B and 10C, each one of which carries a different type of scent-emitting oil 13A, 13B, and 13C. Each one of these scent-emitting oils 13 emits a different scent.

As can be noted from FIG. 5, the box 1 includes a longitudinal transverse slot 14 on the top 2. A manual slide 15 is adapted to be inserted in this slot 14, so as to selectively block the air-current flowing through the scent-carrying pipe arrangement 10 and the outlet pipe 12, by way of the action of the pump or blower 9. The blocking of the scent-carrying air flow can be effected in several ways. A slide 16, having a handle 17, (see FIG. 3B) may be inserted into the longitudinal slot 14. This slide is of a configuration and dimensions so as to block one or two of the pipes 10a, 10b, and 10c of the pipe arrangement 10. For example, two slides 16 (FIG. 3B) may be inserted to selectively block two pipes of the pipe arrangement 10 (see FIG. 3A). Alternatively, a slide 16B, having an orifice 18, may be inserted into the slot 14 and can be moved, so as to bring the orifice 18 into coincidence with one of the pipes 10a or 10c, by simply turning the slide 16b by 180° (FIG. 3C). In this manner, the pipe 10a or 10c can be selectively unblocked by bringing into coincidence the orifice 18 with the open cross section of the pipe 10a or 10c. In order to unblock the pipe 10b, an alternative slide (not illustrated) would be used in conjunction with two slides of the type shown in FIG. 3B, which would have the orifice 18 centrally located on the slide. By providing such an arrangement, it is possible to select one of several scents, which would then be blown out and expelled through the fragrance porthole 6. For each fragrance, a particular, preselected photograph would be mounted on the display stand support 3.

It is, of course, possible to simply provide one scent-emitting oil in one scent-conducting pipe (see FIG. 1A). In such a simplified construction, no slot 14 and slide 16 would be necessary, as the single scent-emitting oil would simply be mounted on a straight pipe 10, having an air inlet 11, and being directly connected via an outlet portion 12 with the pump of blower 9, so that the scent-carrying air stream would be ejected from the fragrance porthole 6 simply by simultaneously turning on the tape recorder and player 8 and the pump or blower 9.

It is, of course, possible to provide, in lieu of an actuating button, a photocell-light beam actuating mechanism 7, 7' which automatically turn on the tape recorder and player 8 and the blower 9. The activation of the tape recorder and player 8 and blower 9 automatically ceases after a predetermined period of time. Actuating is effected upon interruption of the light beam path between light source 7' and photocell 7 by a potential customer passing therebetween.

In the event a pump is used in lieu of a blower, the most suitable type of pump is a diaphragm pump which would expel the scent-containing air by means of pump strokes, so that such scent carrying air would be expelled in rapidly sequential air pulses or bursts.

The arrangement of this invention ma be embodied in other specific forms, without departing from the spirit or essential attributes thereof. Accordingly, reference should be made to the appended claims rather than to the foregoing specification as indicated in the scope of the invention.

What is claimed is:

1. A scent and audio display unit comprising:
(a) a housing having a front wall in which a loudspeaker and fragrance porthole are operatively mounted;
(b) fragrance emitting and sound emitting means operatively mounted in said housing, said sound emitting means being in the form of a tape player which plays a prerecorded magnetic tape;
(c) an electrical power source operatively connected to said fragrance emitting and sound emitting means; and
(d) activating means operatively mounted on said housing and being connected to said electrical power source for simultaneously activating or deactivating said fragrance and sound emitting means by selectively connecting and disconnecting said fragrance emitting and sound emitting means from said electrical power source.

2. The scent and audio display unit as set forth in claim 1, wherein said housing has a top wall, a display stand support is mounted on said top wall and is adapted to support a preselected photo display.

3. The scent and audio display unit as set forth in claim 1, wherein said activating means includes an actuating button which is centrally mounted on said front wall.

4. The scent and audio display unit as set forth in claim 1, wherein said fragrance emitting means include pipe means;
a fragrance emitting composition mounted in said pipe means;
blower means in communication with said pipe means, and said fragrance porthole for blowing out a fragrance containing air stream through said porthole.

5. The scent and audio display unit as set forth in claim 4, wherein said pipe means include an inlet pipe and an outlet pipe, said outlet pipe being in communication with said blower means;
a plurality of branch pipes being disposed between such inlet and outlet pipes, the opposite ends of said plurality of branch pipes being respectively connected to said inlet and outlet pipes;

said housing having a top wall, a longitudinal slot on said top wall, each one of said branch pipes having a transverse slot in alignment with said longitudinal slot; and slide means adapted to be slidably inserted in said slots to selectively block one or more of the bores defined by said branch pipes to selectively block the flow of fragrance containing air therethrough.

6. The scent and audio display unit as set forth in claim 5, wherein said blower means includes a diaphragm pump adapted to expel scent containing air bursts.

7. The scent and audio display unit as set forth in claim 1, wherein said activating means includes a photocell and a light beam source which automatically activate and deactivate said fragrance and sound emitting means upon the interruption of the light beam path between said photocell and light beam.

8. The scent and audio display unit as set forth in claim 1, wherein said electrical power source is an electrical battery.

9. A scent and audio display unit comprising:
(a) a housing having a front wall in which a fragrance porthole is operatively mounted;
(b) fragrance emitting and sound emitting means operatively mounted in said housing, said sound emitting means being in the form of a tape player which plays a prerecorded magnetic tape;
(c) a loudspeaker operatively connected to said sound emitting means;
(d) an electrical power source operatively connected to said fragrance emitting and sound emitting means; and
(e) activating means operatively mounted on said housing and being connected to said electrical power source for simultaneously activating or deactivating said fragrance and sound emitting means by selectively connecting and disconnecting said fragrance emitting and sound emitting means from said electrical power source.

* * * * *